United States Patent
Kruger et al.

(10) Patent No.: US 7,652,468 B2
(45) Date of Patent: Jan. 26, 2010

(54) CORRECTION OF MEASURED VALUES FOR A MAGNETIC LOCALIZATION DEVICE

(75) Inventors: Sascha Kruger, Hamburg (DE); Hans-Aloys Wischmann, Henstedt-Ulzburg (DE); Holger Timinger, Hamburg (DE); Jorg Sabczynski, Norderstedt (DE); Jorn Borgert, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 364 days.

(21) Appl. No.: 10/598,013

(22) PCT Filed: Feb. 11, 2005

(86) PCT No.: PCT/IB2005/050530

§ 371 (c)(1), (2), (4) Date: Aug. 16, 2006

(87) PCT Pub. No.: WO2005/082247

PCT Pub. Date: Sep. 9, 2005

(65) Prior Publication Data

US 2008/0157755 A1   Jul. 3, 2008

(30) Foreign Application Priority Data

Feb. 18, 2004 (EP) .................... 04100639

(51) Int. Cl.
*G01B 7/0004* (2006.01)
*G01B 7/14* (2006.01)
*A61B 5/05* (2006.01)

(52) U.S. Cl. .................. 324/207.12; 600/424; 600/117; 702/150; 702/95

(58) Field of Classification Search ................ 324/207.12–207.25, 225; 702/94–95, 150; 600/117, 424
See application file for complete search history.

(56) References Cited

U.S. PATENT DOCUMENTS

| 6,175,756 B1 | 1/2001 | Ferre et al. |
| 6,636,757 B1 | 10/2003 | Jascob et al. |
| 2002/0165448 A1 | 11/2002 | Ben-Haim et al. |
| 2003/0130576 A1 | 7/2003 | Seeley et al. |
| 2003/0216639 A1 | 11/2003 | Gilboa et al. |
| 2008/0174304 A1* | 7/2008 | Anderson ............... 324/207.17 |

FOREIGN PATENT DOCUMENTS

| WO | 01/63312 A1 | 8/2001 |
| WO | 2004/096042 A1 | 11/2004 |

* cited by examiner

*Primary Examiner*—Jay M Patidar

(57) ABSTRACT

The invention relates to a device and a method for correction of the position (x) of a field sensor (4) measured by means of a magnetic localization device. External field distortions, such as caused for example by the rotating components (1a, 1b) of a computer tomograph (1), are then determined with the help of reference sensor (3) placed at a known position. It is possible to deduce, for example, the current angle of rotation (Φ) of the computer tomograph (1) from the measurement signals of the reference sensor (3). Based on an empirically determined correction (δ(x, Φ)), the uncorrected determined positions (x) of the field sensor (4) can then be converted to corrected positions (x') in relation to the field distortions. The field generator (2) and the reference sensor (3) are preferably fastened to the gantry in order to eliminate the dependency of the field distortions on an inclination of the gantry.

13 Claims, 1 Drawing Sheet

CORRECTION OF MEASURED VALUES FOR A MAGNETIC LOCALIZATION DEVICE

The invention relates to a magnetic localization device comprising a field generator and a field sensor, an examination device with such a localization device as well as a method for position measurement with such a magnetic localization device.

Magnetic localization devices are used especially in medical examinations to determine the position of instruments such as a catheter in a patient's body, without requiring constant X-ray radiation for this purpose. What is problematic here, however, is that the location measurements of such localization devices can be easily hampered by external magnetic fields or distortions of the measuring field. In this context, there is proposed in U.S. Pat. No. 6,636,757 B1 to position the field generator adjacent a shield at known distorting objects, such as metallic devices, such that the field distortion is suppressed and any movements of the distortion source are followed. The disadvantage here is, however, that it is necessary to intervene in the design of the imaging devices, involving high expenditure, giving rise to additional costs and making post-fitting of existing systems difficult.

Against this background, it was an object of the present invention to provide means for facilitating correction for external field distortions in a magnetic localization device.

The magnetic localization device as invented comprises the following components:
a) A field generator for the generation of a magnetic field. The field here is typically inhomogeneous in space and/or time according to a known functional correlation, so that the position of a certain spatial point relative to the field generator can be deduced from the magnitude (value, vector or vector components) of the field.
b) At least one field sensor for the measurement of the magnetic field generated by the field generator. As a rule, the field sensor is placed on an object to be observed, such as a catheter, as a localizer while the field generator is at a known, typically stationary point in space. In this constellation, the place of the field sensor thus corresponds to the position searched for. Nevertheless, it is also possible to interchange the roles of the field sensor and field generator and to determine the location of the field generator in relation to the (known) location of the field sensor.
c) A reference sensor for measuring the magnetic field at a known reference position. The "reference position" should then be known with respect to the one of the two components of field generator and field sensor whose position is also assumed to be known. In the typical situation of a securely mounted field generator, the position of the reference sensor in relation to the field generator is thus known.
d) A control unit, which can be realized, for example, by using a microcomputer with appropriate software and which is arranged for determining the position of the field sensor relative to the field generator (which is the same thing as determination of the position of the field generator relative to the field sensor) and thereby to compensate the external field distortions of the magnetic field by taking reference sensors into consideration. Suitable methods for carrying out such compensation are explained in detail in the context of preferred embodiments.

The advantage of the described magnetic localization device is that it allows in a simple way to correct external field distortions. This can be done by measuring the signals of a reference sensor, so that the field distortions can be deduced by comparing the position of the reference sensor thus determined with its known, real position. This information can in turn be used for the desired compensation of the measured relative position of the field sensor.

The localization device is especially suitable for use in combination with X-ray computer tomography (CT), because considerable dynamic field distortions are generated by the rotating components (tube, detector). Optionally, in this case, the field generator and/or the reference sensor are fastened to the gantry of the computer tomograph. Preferably, both parts are fastened to the gantry, so possible inclination movements of the gantry are copied by them synchronously and thus there is no relative change in the path of the field.

The control unit preferably has a memory, in which a calibration function is stored, which provides a correction shift for the field sensor position determined without correction for external field distortions (directly or not directly), depending on the measured signals of the reference sensor and the field sensor. The addition of this correction shift to the uncorrected position of the field sensor determined by the conventional methods provides an exact estimate for the real position of the field sensor, in which particularly external field distortions have been corrected.

Furthermore, the invention relates to an examination device which comprises the following components:
An imaging device, for example an X-ray device, an MR device, an ultrasonic device or suchlike. This is typically an imaging device that by itself or through its accessories generates considerable field distortion. In particular, this may be a computer tomograph, which causes dynamic magnetic field distortions due to the rotation of its components.
A magnetic localization device of the type described above, that is to say, with at least a field generator, at least a field sensor, a reference sensor and a control unit, which corrects the position of the field sensor relative to the field generator, taking into consideration the measurement of the reference sensor.

Furthermore, the invention relates to a method for position measurement with a magnetic localization device, which method comprises the following steps of:
a) collecting the signals from a field sensor and/or a field generator. The signals from a field generator describe the current magnetic field generated by this generator, for example in the form of currents in the excitation coils of the field generator. The signals from the field sensor, on the other hand, measure the magnitude (value, vector or vector components) of a magnetic field at a certain spatial point at which the field sensor is located.
b) collecting the signals from a magnetic reference sensor, which is installed at a known spatial position relative to the field generator or to the field sensor. The expression "magnetic reference sensor" should be viewed as a common name for a magnetic field sensor, whose signals reflect the magnitude of the magnetic field and are used as reference magnitudes.
c) determining the position of the field sensor relative to the field generator (in other words the relative position between field sensor and field generator), where external field distortions of the magnetic field are compensated by taking the signals from the reference sensor into consideration. In this manner, particularly the absolute spatial position of the field sensor can also be determined, if that of the field generator is assumed to be known.

The method relates in general to the steps that can be executed with a localization device of the type described above. With respect to details, advantages and further features, reference is made to the above description.

According to a preferred embodiment of the method, a correction function is determined, which indicates a correction shift for said uncorrected position of the field sensor based on the signal of the reference sensor and of the uncorrected determined position of the field sensor. The uncorrected position of the field sensor is determined by the conventional methods. The position of the field sensor may particularly be concluded from the (known) field configuration of the field generator. The implicit assumption here is that the field configuration generated by the field generator is undistorted. As this generally does not conform to reality, a correction shift is additionally determined, which is to be added to the uncorrected position of the field sensor to obtain a better estimate for the real position of the field sensor.

According to a further aspect of the above-mentioned method, the correction function is first empirically determined for the support points in a volume of interest, i.e. through measurements of the field present there with the help of a probe sensor, whose actual spatial position is re-measured exactly in each case by using other means as well as by parallel measurement of the signals of the reference sensor. The information available for the support points (measured and real position of the probe sensor, reference sensor signal) is then extended by extrapolation or interpolation on the entire volume of interest, in order to obtain a roughly valid correction function in this manner.

Furthermore, a (uni- or multidimensional) parameter can be determined from the measurement signal of the reference sensor, which characterizes the external field distortion. This parameter can then be used as a variable in the above-mentioned correction function, to reflect the effect of the reference sensor there.

The above-mentioned parameter can especially describe the angle of rotation of a computer tomograph that is situated in the vicinity of the localization device. It is seen that the field distortions exerted by such a computer tomograph are primarily dependent on the angle of rotation, because important field-generating or field-distorting components, such as the detector area, rotate along with the computer tomograph. If necessary, the functional correlation between the signals from the reference sensor and the angle of rotation can also be determined empirically or adaptively.

The invention will be explained below by way of example with the help of attached figures. In the drawings, FIG. 1 shows schematically the components of an examination device as invented;

Figure 1:
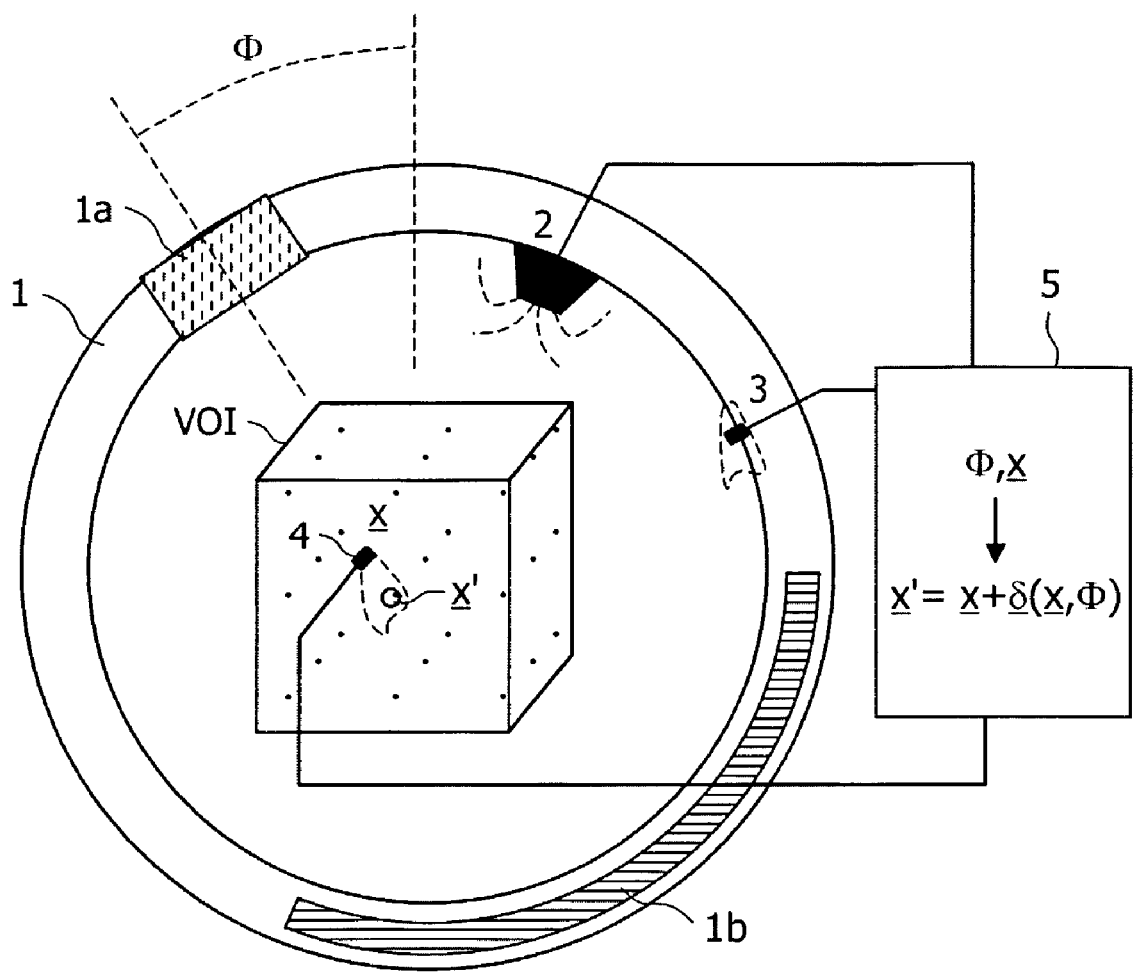

The situation shown in FIG. 1 relates to the case where a magnetic localization device is used in combination with a computer tomograph 1. This is a typical and important application, though the usability of the invention is by no means restricted to it.

The computer tomograph 1 usually comprises a circular gantry, in which an X-ray source 1a as well as an X-ray detector 1b opposite to it are supported such that they can be rotated by the angle of rotation $\Phi$ with respect to the central axis of the device. Two-dimensional section images or three-dimensional volume data can be generated by the computer tomograph 1 from a volume of interest VOI inside the ring.

Furthermore, a magnetic localization device is available which contains a field generator 2 for generating a temporally and spatially inhomogeneous magnetic field in the volume of interest VOI as well as a field sensor 4. The field sensor 4 measures the size of the magnetic field generated by the field generator 2, thus making it possible to deduce its position x (with a known position of the field generator 2) in this manner. The field sensor 4 can, for example, be fixed to the tip of a catheter (not shown), which is to be navigated in the vascular system of a patient. The position of the field sensor 4 determined with the help of the localization device can then be used, for example, so as to represent the current position of the catheter on a (static) vessel map.

Furthermore, the field generator 2 as well as the field sensor 4 is linked to a control unit 5 (for example a microcomputer). The required calculations for determining the (uncorrected) position x of the field sensor 4 take place in the control unit 5.

In the method described so far, one encounters the problem that the determined position of the field sensor 4 is erroneous owing to distortions of the magnetic field. Such distortions particularly arise owing to the X-ray source 1a as well as the detector 1b of the computer tomograph 1, where the distortions dynamically change with the current angle of rotation $\Phi$ of the computer tomograph 1.

Figure 2:
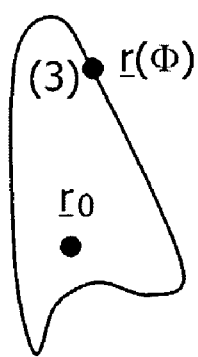
FIG. 2 shows the trajectory of an apparent movement of the reference sensor caused by field distortions.

In order to improve the accuracy of localization of the field sensor 4 in view of this situation, it is proposed here to use a reference sensor 3, which is placed at a known position relative to the field generator 2. Due to the dynamic distortions of the magnetic field owing to the rotation of the computer tomograph 1, the measured position of the reference sensor 3 apparently moves on a closed trajectory $\underline{r}(\Phi)$, which is shown in FIG. 2 together with the real position $\underline{r}_0$ of the reference sensor 3. The correlation $r(\Phi)$ between the angle of rotation and the apparent position $\underline{r}$ can for example be determined empirically and then inverted, so as to determine the relevant angle of rotation $\Phi$ of the computer tomograph 1 from a measurement signal of the reference sensor 3 (that is to say, of an apparent position $\underline{r}$). Determining the angle of rotation $\Phi$ in this way does not require any intervention in the inner routines of the computer tomograph.

Figure 3:
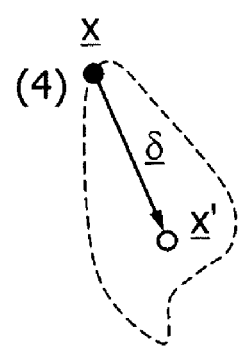
FIG. 3 shows the corresponding trajectory for the field sensor together with the determined correction shift $\delta$ of a measured position x.

The current angle of rotation $\Phi$ can be calculated from the measurement signals of the reference sensor 3 by connecting the reference sensor 3 to the control unit 5. This information can then also be used for correcting the (uncorrected) position measurement value x of the field sensor 4 in relation to the rotation of the computer tomograph 1. A correction function $\delta(x, \Phi)$ is thereby preferably used for the correction, where the corrected position x' of the field sensor 4 is calculated from its uncorrected position x by the formula $x'=x+\delta(x, \Phi)$. This correlation is shown in FIG. 3 for the apparent trajectory of the field sensor 4.

The correction function $\delta(x, \Phi)$ can, for example, be determined empirically, if the apparent trajectory $\underline{r}(\Phi)$ of the reference sensor 3 shown in FIG. 2 is plotted simultaneously with the measured values of a probe field sensor, which is successively placed at known grid positions in the volume of interest VOI. As a probe field sensor can be used, for example, the field sensor 4, where it could preferably simultaneously measure the magnetic field in three spatial directions. The position of the grid positions is to be selected sufficiently close in view of the magnetic field distortions taken as the basis. By interpolation or extrapolation respectively of the values on the grid positions (support points), the correction function $\delta(x, \Phi)$ searched for can then be determined in the whole volume VOI.

As can further be seen in the FIG. 1, the field generator 2 as well as the reference sensor 3 is preferably fastened to the gantry 1. The advantage of this is that possible inclinations of the gantry are simultaneously followed by both components, so that inclination-related changes in the field distortions caused by the CT 1 have no effect on the localization system.

An additional calibration in relation to the angle of inclination of the CT 1 is therefore not necessary and the measurements of the localization system are carried out in the coordinate system of the gantry 1.

The invention claimed is:

1. A magnetic localization device, comprising:
   a) a field generator for generating a magnetic field;
   b) a field sensor for measuring the magnetic field;
   c) a reference sensor for measuring the magnetic field at a known reference position; and
   d) a control unit, which is arranged for determining a position of the field sensor relative to the field generator and thereby compensating for external field distortions by taking the reference sensor into consideration and correcting the determined position of the field sensor if external field distortions are present.

2. A localization device as claimed in claim 1, wherein the spatial position of the field generator is known.

3. A localization device as claimed in claim 1, wherein at least one of the field generator and the reference sensor is fastened to the gantry of a computer tomograph.

4. A localization device as claimed in claim 1, wherein the control unit contains a memory with a calibration function, which provides a correction shift for an uncorrected determined position of the field sensor based on measured signals of the reference sensor and the field sensor.

5. A localization device as claimed in claim 4, wherein the correction shift is further based on empirical measurements taken with a probe sensor at one or more support points in a volume of interest.

6. A localization device as claimed in claim 4, wherein the measured signals of the reference sensor are used to determine a correction parameter describing an angle of rotation of a computer tomograph situated in the vicinity of the localization device.

7. A method for position measurement with a magnetic localization device, comprising the steps of:
   a) collecting the signals of at least one of a field sensor and a field generator;
   b) collecting the signals of a magnetic reference sensor, which is placed at a known spatial position relative to the field generator or to the field sensor; and
   c) determining a position of the field sensor relative to the field generator, where external field distortions are compensated for by taking the signals of the reference sensor into consideration and correcting the determined position of the field sensor if external field distortions are present.

8. A method as claimed in claim 7, wherein a correction function is determined, which indicates a correction shift for an uncorrected determined position of the field sensor in dependence on the signal of the reference sensor and the uncorrected determined position of the field sensor.

9. A method as claimed in claim 8, wherein the correction shift further depends on empirical measurements taken with a probe sensor at one or more support points in a volume of interest.

10. A method as claimed in claim 8, wherein the signal of the reference sensor is used to determine a correction parameter describing an angle of rotation of a computer tomograph situated in the vicinity of the localization device.

11. A method as claimed in claim 7, wherein a parameter is determined from the signal of the reference sensor, which parameter characterizes the external field distortion.

12. A method for position measurement with a magnetic localization device, comprising the steps of:
    a) collecting the signals of at least one of a field sensor and a field generator;
    b) collecting the signals of a magnetic reference sensor, which is placed at a known spatial position relative to the field generator or to the field sensor;
    c) determining the position of the field sensor relative to the field generator, where external field distortions are compensated for by taking the signals of the reference sensor into consideration;
    d) wherein a correction function is determined, which indicates a correction shift for an uncorrected determined position of the field sensor in dependence on the signal of the reference sensor and the uncorrected determined position of the field sensor; and
    e) wherein the correction function for support points in a volume of interest is empirically determined and extended by extrapolation or interpolation respectively on the whole volume.

13. A method for position measurement with a magnetic localization device, comprising the steps of;
    a) collecting the signals of at least one of a field sensor and a field generator;
    b) collecting the signals of a magnetic reference sensor, which is placed at a known spatial position relative to the field generator or to the field sensor;
    d) determining the position of the field sensor relative to the field generator, where external field distortions are compensated for by taking the signals of the reference sensor into consideration;
    d) wherein a parameter is determined from the signal of the reference sensor, which parameter characterizes the external field distortion; and
    e) wherein the parameter describes the angle of rotation of a computer tomograph situated in the vicinity of the localization device.

* * * * *